United States Patent
Xu et al.

(10) Patent No.: US 11,839,515 B2
(45) Date of Patent: Dec. 12, 2023

(54) DETECTION, PRESENTATION AND REPORTING OF B-LINES IN LUNG ULTRASOUND

(71) Applicant: KONINKLIJKE PHILIPS N.V., Eindhoven (NL)

(72) Inventors: Jingping Xu, Shanghai (CN); Balasundar Iyyavu Raju, North Andover, MA (US); Shougang Wang, Ossining, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 138 days.

(21) Appl. No.: 16/640,506

(22) PCT Filed: Aug. 17, 2018

(86) PCT No.: PCT/EP2018/072370
§ 371 (c)(1),
(2) Date: Feb. 20, 2020

(87) PCT Pub. No.: WO2019/038210
PCT Pub. Date: Feb. 28, 2019

(65) Prior Publication Data
US 2021/0068789 A1 Mar. 11, 2021

(30) Foreign Application Priority Data
Aug. 21, 2017 (WO) ................ PCT/CN2017/098272
Nov. 13, 2017 (EP) ..................................... 17201269

(51) Int. Cl.
*A61B 8/08* (2006.01)
*A61B 8/00* (2006.01)

(52) U.S. Cl.
CPC ............ *A61B 8/5207* (2013.01); *A61B 8/085* (2013.01); *A61B 8/461* (2013.01)

(58) Field of Classification Search
CPC ........ A61B 8/5207; A61B 8/085; A61B 8/461
See application file for complete search history.

(56) References Cited

U.S. PATENT DOCUMENTS 5,293,870 A * 3/1994 Ophir .................. G01S 7/52036
600/437
6,443,896 B1 9/2002 Detmer
(Continued)

FOREIGN PATENT DOCUMENTS

WO 2017162860 A1 9/2017

OTHER PUBLICATIONS

Shaffie, Ahmed, et al. "A generalized deep learning-based diagnostic system for early diagnosis of various types of pulmonary nodules." Technology in cancer research & treatment 17 (2018): 1533033818798800.*
(Continued)

*Primary Examiner* — Joseph M Santos Rodriguez
*Assistant Examiner* — Amy Shafqat

(57) ABSTRACT

The present disclosure describes an ultrasound imaging system configured to identify and display B-lines that may appear during ultrasound scanning of a chest region of a subject. In some examples, the system may include an ultrasound probe and at least two processors configured to generate a plurality of image frames from ultrasound echoes received at the probe. The processors may be further configured to identify a pleural line in each of the plurality of image frames, define a region of interest below each pleural line, identify one or more candidate B-lines within the region of interest, identify one or more B-lines by evaluating one or more parameters of each candidate B-line, and select a target image frame from the plurality of image frames by identifying an image frame that maximizes at least a number or an intensity of B-lines.

15 Claims, 10 Drawing Sheets

(56) References Cited

U.S. PATENT DOCUMENTS

| | | | |
|---|---|---|---|
| 6,530,885 | B1 | 3/2003 | Entrekin et al. |
| 11,446,008 | B2 * | 9/2022 | Mehanian ............... G06F 17/18 |
| 2010/0234716 | A1 | 9/2010 | Engel |
| 2015/0002538 | A1 | 1/2015 | Sohn et al. |
| 2015/0150503 | A1 | 6/2015 | Pamnani et al. |
| 2015/0297188 | A1 * | 10/2015 | Konofagou ............... A61B 8/08 600/442 |
| 2015/0374341 | A1 * | 12/2015 | Chen .................. G01S 15/8977 600/443 |
| 2017/0071577 | A1 * | 3/2017 | Seo ..................... G01S 7/52071 |
| 2017/0086790 | A1 * | 3/2017 | Halmann ............. A61B 8/0858 |
| 2019/0105013 | A1 * | 4/2019 | Wang .................... A61B 8/463 |
| 2020/0352547 | A1 * | 11/2020 | Raju ...................... A61B 8/461 |

OTHER PUBLICATIONS

PCT/EP2018/072370 ISR & WO, dated Sep. 25, 2018, 16 Page Document.

Anderson et al: "Inter-Rater Reliability of Quantifying Pleural B-Lines Using Multiple Counting Methods"; J Ultrasound Med 2013, vol. 32, pp. 115-120.

Brattain et al: "Automated B-Line Scoring On Thoracic Sonography"; J Ultrasound Med 2013, vol. 32, pp. 2185-2190.

Byrne et al: "Ultrsound in the Critically Ill"; Ultrasound Clin 6 (2011) pp. 235-259.

Enghard et al: "Simplified Lung Ultrasound Protocol Shows Excellent Prediction of Extravascular Lung Water in Ventilated Intensive Care Patients"; Critical Care 92015), 19:36, pp. 1-8.

Gullett et al: "Interobserver Agreement in the Evaluation of B-Lines Using Bedside Ultrasound"; Journal of Critical Care 30 (2015), pp. 1395-1399.

Manson et al: "Identification of Sonographic B-Lines With Linear Transducer Predicts Elevated B-Type Natriuretic Peptide Level"; Western Journal of Emergency Medicine: Integrating Emergency Care With Population Health 12 (1), 2011, pp. 102-106.

Moshavegh et al: "Novel Automatic Detection of Pleura and B-Lines (Comet-Tail Artifacts) On In-Vivo Lung Ultrasound Scans"; Medical Imaging 2016: Ultrasonic Imaging and Tomography, Proc. of SPIE, vol. 9790, pp. 97900K-1-97900K-7.

Picano et al: "Ultrasound Lung Comets: A Clinically Useful Sign of Extravascular Lung Water"; American Society of Echocardiography, 2006, pp. 356-363.

Picano et al: "Ultrasound of Extravascular Lung Water: A New Standard for Pulmonary Congestion"; European Heart Journal (2016), vol. 37, pp. 2097-2104.

Weitzel et al: "Quantitative Lung Ultrasound Comet Measurement:Method and Initial Clinical Results"; Blood Purif, 2015, vol. 39, pp. 37-44.

* cited by examiner

508

| Zone number | Number of B-lines | B-line score (1 to 10) |
|---|---|---|
| 1 | 1 | 1 |
| 2 | 0 | 0 |
| 3 | 4 | 6 |
| 4 | | |
| 5 | | |
| 6 | | |
| 7 | | |
| 8 | | |

FIG. 5C

DETECTION, PRESENTATION AND REPORTING OF B-LINES IN LUNG ULTRASOUND

RELATED APPLICATION

Cross-Reference to Prior Applications

This application is the U.S. National Phase application under 35 U.S.C. § 371 of International Application No. PCT/EP2018/072370, filed on Aug. 17, 2018, which claims the benefit of Chinese Patent Application No. PCT/CN2017/098272, filed on Aug. 21, 2017 and European Patent Application No. 17201269.2, filed on Nov. 13, 2017. These applications are hereby incorporated by reference herein.

Technical Field

This application pertains to ultrasound imaging and more specifically to systems and methods for detecting B-lines in images of the lungs, evaluating B-lines across multiple image frames, and displaying B-line information.

BACKGROUND

Lung ultrasound can be performed by positioning the ultrasound transducer both longitudinally, perpendicular to the ribs, and obliquely, along the intercostal spaces. Among the various features evaluated via lung ultrasound to diagnose conditions such as pneumothorax ("PTX"), pneumonia, pulmonary edema and others, are visual artifacts known as B-lines. B-lines are discrete/fused vertical hyperechoic reverberations that typically extend downward, e.g., closer to maximum imaging depth, from the pleural line, which marks the interface between the chest wall and the lung. B-line scoring may be critical to characterizing lung diseases, diagnosing PTX, and also estimating extravascular lung water, which may be indicative of several lung conditions. As such, inaccurate B-line assessment may lead to inaccurate diagnoses and evaluation of lung conditions. Identifying B-Lines may be difficult and time-consuming for dynamic frame-to-frame live imaging, especially for inexperienced users manipulating an ultrasound probe while subjectively interpreting and manually counting B-lines within each ultrasound image from lung ultrasound image sequences. Techniques for a more precise, user-friendly approach to detect and/or display B-lines may be desired in a wide range of medical settings, e.g., clinical applications at emergency treatment centers, intensive care units ("ICU"), and critical care units, to name a few.

SUMMARY

Provided herein are ultrasound systems and methods for improved B-line detection and assessment in the lungs. Various examples involve systems configured to receive and evaluate ultrasound echoes embodied in a plurality of image frames to identify and display a target image frame containing the most and/or brightest B-lines. In some examples, the target frame could be used as a frame of reference, e.g., a representation, in final reporting to end-users, indicating when and where (left or right side, upper or lower) the maximum B-line event happens. This information may add value in clinical reports for quick decision-making in emergency situations. Systems may include an ultrasound probe configured to receive ultrasound echoes, a signal processor configured to generate a plurality of image frames, and a data processor configured to identify a pleural line and region of interest proximate, e.g., below, each pleural line. Within each region of interest, the data processor may be configured to identify one or more candidate B-lines. Candidates may be excluded or selected as legitimate B-lines by evaluating one or more parameters, which may include a level of intensity uniformity, a coherent line length, a starting location, and/or an ending location of each candidate B-line. Systems may also include a user interface configured to display target image frames and various B-line characteristics determined by the data processor operating in tandem with the ultrasound probe. The systems disclosed herein may be automated and performed in real time, thereby reducing examination time and interpretive error.

In accordance with some examples, an ultrasound imaging system may include an ultrasound probe configured to receive ultrasound echoes from a subject to image a lung region of the subject. At least two processors may be in communication with the ultrasound probe. The processors may be configured to generate a plurality of image frames from the ultrasound echoes; identify a pleural line in each of the plurality of image frames; define a region of interest below each pleural line; identify one or more B-lines from one or more candidate B-lines within the region of interest by evaluating one or more parameters of each candidate B-line; and select a target image frame from the plurality of image frames by identifying an image frame that maximizes an intensity of identified B-lines.

In some examples, the one or more parameters may include at least one of a level of intensity uniformity, a length, a starting location, an ending location, or a level of motion detected across multiple image frames. Example systems may further include a user interface in communication with at least one of the processors. The user interface may be configured to display the target image frame simultaneously with a real-time image responsive to the ultrasound echoes received at the ultrasound probe. In some embodiments, the user interface may be configured to display the target image frame adjacent to the real-time image such that the target image frame does not overlap with the real-time image. In some examples, the user interface may be configured to display two or more sub-regions selectable by a user, each sub-region corresponding to a portion of the lung region of the subject. In various embodiments, the processors may be configured to identify one or more B-lines and a target frame within each sub-region. In some embodiments, the user interface may be configured, for each sub-region, to display one or more of a number of B-lines, an indication of whether the number of B-lines exceeds a pre-determined threshold, e.g., less or equal to three B-lines per scan, and/or a starting and ending location of each B-line. In some embodiments, the processors may be configured to determine a number of B-lines and/or a B-line score for each sub-region. The B-line score may be based at least in part on a level of B-line coverage within at least one intercostal space present within each sub-region. In some embodiments, the user interface may be configured to provide an indication of a number of B-lines, a B-line score, and/or an indication of whether the B-line score is normal or abnormal for each sub-region such that a distribution of B-lines throughout the chest (e.g., lung region) is displayed. In various embodiments, the user interface may be configured to receive an indication of a location of the ultrasound probe with respect to the lung region of the subject.

In some examples, the intensity of B-lines includes at least one of a number of B-lines, a width of one or more B-lines, or a B-line score, the B-line score based at least in part on a level of B-line coverage within at least one intercostal space present within the region of interest. In some embodiments, the processors may be configured to identify one or more candidate B-lines by generating an axial projection ("AP") curve within the region of interest. In some embodiments, the processors may be configured to generate multiple AP curves and identify the one or more candidate B-lines based on one or more coefficients associated with one or more of the multiple AP curves. For example, the processors may be configured to generate two or more sub-AP curves within two or more sub-locations within the region of interest and determine a normalized cross correlation coefficient between each of the sub-AP curves and the AP curve or between every adjacent two sub-AP curves (for example: sub-AP curve at index n and sub-AP curve at index (n+1)).

A method in accordance with the present disclosure may involve acquiring image data of a region of a lung tissue via an ultrasound probe; generating a plurality of image frames from the image data; identifying a pleural line in each of the plurality of image frames; defining a region of interest below each pleural line; identifying one or more B-lines from one or more candidate B-lines within the region of interest by evaluating one or more parameters of each candidate B-line; and selecting a target image frame from the plurality of image frames by selecting an image frame that maximizes an intensity of B-lines.

In some embodiments, the method may further involve displaying the target image frame simultaneously with a real-time image of the lung tissue. In some embodiments, the method may also involve comparing two or more image frames to detect motion of one or more candidate B-lines. In various embodiments, the one or more parameters may include at least one of an intensity uniformity level, a length, a starting location, an ending location, or a level of the motion detected.

In some examples, the method may further involve identifying an intercostal space between at least one pair of ribs within the region of interest; determining a proportion of the intercostal space covered by one or more B-lines; and generating a B-line score based on the proportion. In some embodiments, the method further involves generating and displaying a pictorial representation of multiple B-line scores, each B-line score corresponding to a sub-region within the region of the lung tissue. In some examples, the B-line scores corresponding to one or more sub-regions may be added up to compute total B-line score for the subject.

Additionally, any of the techniques for selecting and/or displaying a target image frame may be embodied in executable instructions stored on non-transitory computer-readable medium, which when executed cause a processor or a medical imaging system to be programmed to perform the processes embodied in the non-transitory computer-readable medium.

BRIEF DESCRIPTION OF THE DRAWINGS

FIG. 5C is a table reporting a quantitative B-line score for each region of interest shown in FIG. 5A;

DETAILED DESCRIPTION

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

The present technology is also described below with reference to block diagrams and/or flowchart illustrations of methods, apparatus (systems) and/or computer program products according to the present embodiments. It is understood that blocks of the block diagrams and/or flowchart illustrations, and combinations of blocks in the block diagrams and/or flowchart illustrations, may be implemented by computer executable instructions. These computer executable instructions may be provided to a processor, controller or controlling unit of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

Figure 1:
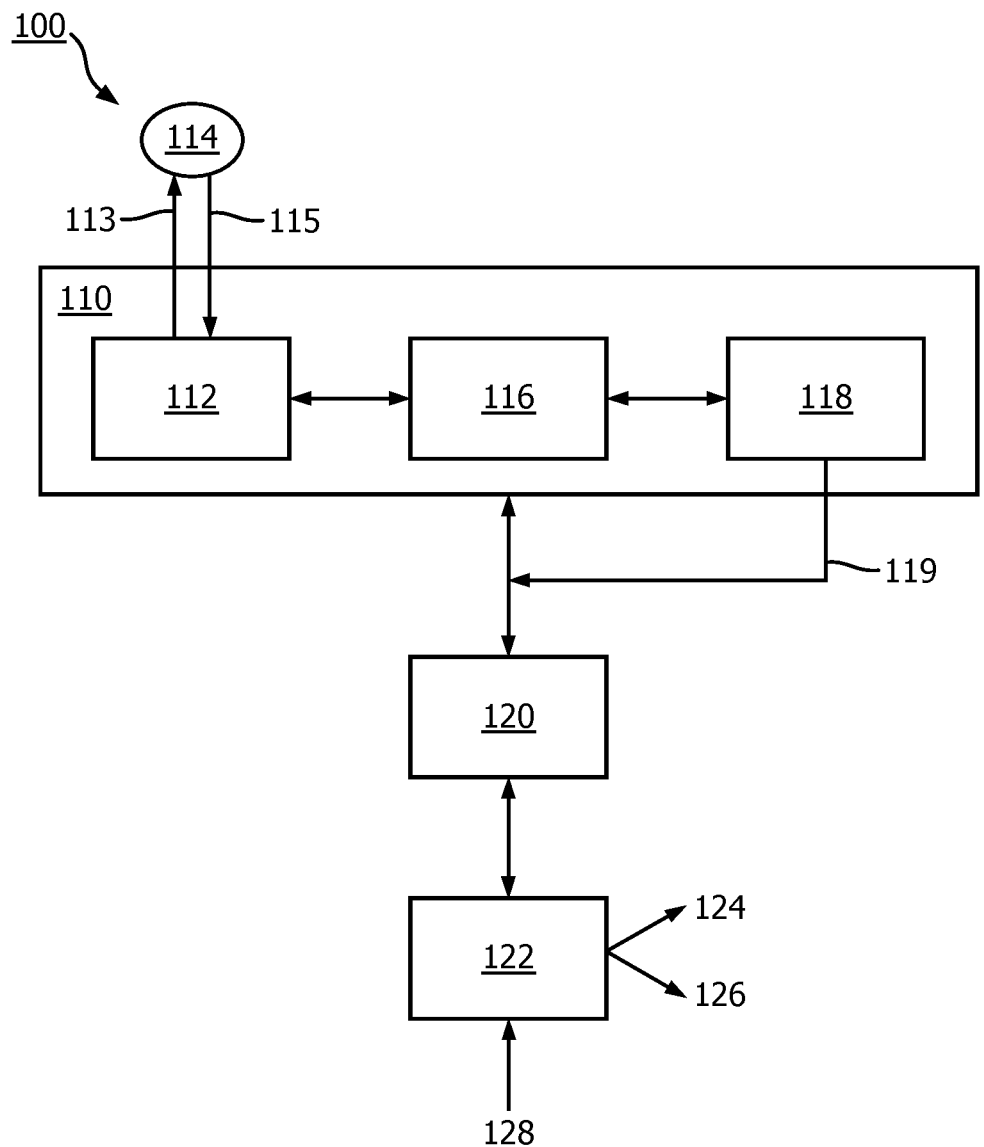
FIG. 1 is a block diagram of an ultrasound imaging system in accordance with the principles of the present disclosure.

FIG. 1 shows an example ultrasound system 100 configured to identify and display a target image frame for visualizing and evaluating B-lines in accordance with the present disclosure. As shown, the system 100 may include an ultrasound data acquisition unit 110. The ultrasound data acquisition unit 110 may include an ultrasound probe which includes an ultrasound sensor array 112 configured to transmit ultrasound signals or beams 113 into a region 114 of a subject, e.g., the lungs, and receive ultrasound signals or echoes 115 responsive to the transmitted beams. As further shown, the ultrasound data acquisition unit 110 may include, in some examples, a beamformer 116 and a signal processor 118, which may be configured to generate a plurality of discrete image frames 119 from the ultrasound echoes 115 received at the array 112. The system 100 may also include a data processor 120, e.g., a computational module or circuitry, configured to detect and evaluate candidate B-lines based on the ultrasound echoes 115 received at the array 112 and processed by the signal processor 118. In some embodiments, the system 100 includes at least one user interface 122 coupled with the data processor 120. The user interface 122 may display various images 124 of the region being scanned, e.g., target image frames containing B-lines, live ultrasound images obtained while the scan is performed, and/or pictorial representations of B-line distributions across a region of the subject being scanned. The user interface 122 may also be configured to display one or more indicators 126, which may embody one or more types of information regarding the existence and/or characteristics of identified B-lines. The user interface 122 may also be configured to receive a user input 128 at any time before, during, or after an ultrasound scan. The configuration of the system 100 shown in FIG. 1 may vary. For instance, the system 100 can be stationary or portable. Various portable devices, e.g., laptops, tablets, smart phones, or the like, may be used to implement one or more functions of the system 100. In examples that incorporate such devices, the ultrasound sensor array 112 may be connectable via a USB interface, for example.

The ultrasound data acquisition unit 110 may be configured to acquire ultrasound data for one or more regions of interest selectable by a user, e.g., a sonographer, clinician or ultrasound technician. According to embodiments of the present disclosure, the region of interest may include a chest region encompassing one or both lungs. The ultrasound sensor array 112 may include at least one transducer array configured to transmit and receive ultrasonic energy. A variety of transducer arrays may be used, e.g., linear arrays, convex arrays, or phased arrays. The number and arrangement of transducer elements included in the sensor array 112 may vary in different examples. For instance, the ultrasound sensor array 112 may include a 1D or 2D array of transducer elements, corresponding to linear array and matrix array probes, respectively. The 2D matrix arrays may be configured to scan electronically in both the elevational and azimuth dimensions (via phased array beamforming) for 2D or 3D imaging. In some examples, a 2D matrix array may be configured to perform sub array beamforming using a microbeamformer, for example as described in U.S. Pat. No. 6,013,032 (Savord), which is incorporated by reference in its entirety herein. One-dimensional arrays may be configured to scan 2D images electronically (via phased array beamforming) or additionally be mechanically swept across a region of interest in an orthogonal direction to the electrically scanned dimension in order to create 3D images.

The data acquisition unit 110 may also include a beamformer 116, e.g., comprising a microbeamformer or a combination of a microbeamformer and a main beamformer, coupled to the ultrasound sensor array 112. The beamformer 116 may control the transmission of ultrasonic energy, for example by forming ultrasonic pulses into focused beams.

The beamformer 116 may also be configured to control the reception of ultrasound signals such that discernable image data may be produced and processed with the aid of other system components. The role of the beamformer 116 may vary in different ultrasound probe varieties. In some embodiments, the beamformer 116 may comprise two separate beamformers: a transmit beamformer configured to receive and process pulsed sequences of ultrasonic energy for transmission into a subject, and a separate receive beamformer configured to amplify, delay, and/or sum received ultrasound echo signals. In some embodiments, the beamformer 116 may comprise a microbeamformer operating on groups of sensor elements for both transmit and receive beamforming, coupled to a main beamformer which operates on the group inputs and outputs for both transmit and receive beamforming, respectively.

As further shown in FIG. 1, at least one processor, such as signal processor 118, may be communicatively, operatively, and/or physically coupled with the sensor array 112. The signal processor 118 included in FIG. 1 is shown as an internal component of the data acquisition unit 110. In some embodiments, the signal processor 118 may comprise a separate component. The signal processor 118 may be configured to receive ultrasound data embodying the ultrasound echoes 115 received at the sensor array 112. From this data, the signal processor 118 may generate a plurality of image frames 119 as a user scans the region 114 of the subject. In operation, the probe containing the ultrasound sensor array 112 may be moved over the surface of the region 114 to collect image data at multiple locations. The user may pause at one or more locations, keeping the sensor array 112 stationary while a series of image frames may be generated based on the ultrasound echoes 115 received at the acquisition unit 110. In this manner, image frames 119 spanning at least one respiratory cycle (preferably two or more cycles if time permits), may be collected at each location examined by the user, which may collectively span the entire chest region, including both lungs. The number of discrete locations may vary depending on the objectives of the user and the clinical setting. For instance, in the ER/ICU setting, about 4 to about 6 locations may be examined, while internal medicine applications may involve a more thorough examination of about 25 to about 35 locations. In various embodiments, the number of locations may range from about 1 to about 40, about 26 to about 34, about 25 to about 30, about 2 to about 30, about 4 to about 20, or about 6 to about 8 locations. By collecting multiple image frames 119 at each location, the system 100 may detect movement and/or changes in the shape of one or more B-lines, each of which may often occur during respiration, as the lungs expand and contract. For instance, discrete B-lines in one frame may fuse during respiration to appear as a single, wider B-line in a subsequent frame.

The number of image frames 119 generated by the signal processor 118 at a given location may vary depending on the ultrasonic pulse rate of the sensor array 112 and the length of time spent at each location. In some examples, the frame (pulse) rate may range from about 20 Hz to about 100 Hz, about 25 Hz to about 80 Hz, about 30 Hz to about 60 Hz, about 35 Hz to about 50 Hz, about 40 to about 48 Hz, or about 42 Hz to about 46 Hz. Higher pulse rates may enable more detailed data collection, such that the number and/or intensity of B-lines contained within the eventually-identified target image frame may be maximized. Accordingly, the pulse rate may be increased for more thorough inspection, which may be necessary to detect small changes in B-line number and/or conformation, and/or transient B-line features that change rapidly during respiration. The length of time spent at each location may also vary, ranging from about 2 to about 6 seconds depending on the respiratory rate of the subject being scanned. The total number of image frames generated at a discrete location may range from about 40 to about 600.

Using the image frames 119 generated by the signal processor 118, the data processor 120 may be configured to perform several operations to identify B-lines and/or select a target image frame for further examination and/or display. For instance, because B-lines begin at the pleural line, the data processor 120 may identify a pleural line in each of the plurality of image frames (if a pleural line is present in each frame). Identifying the pleural line may be necessary, in some examples, to reliably distinguish the B-lines from other hyperechoic features that, while vertically oriented, may not begin at the pleural line. Various pleural line identification techniques may be implemented by the data processor 120 to perform this operation. For instance, the data processor 120, in conjunction with the other components of the system 100, may perform any of the automated processing techniques disclosed in related US patent application titled "Target Probe Placement for Lung Ultrasound" and naming Balasundar et al., which is incorporated by reference in its entirety herein. In some examples, the data processor 120 may additionally evaluate the intensity and/or clarity of the pleural line detected in each image frame, and may compare multiple image frames to prioritize stronger pleural lines for further processing. In some embodiments, the data processor 120 may implement a Hough transform to identify one or more pleural lines. The data processor 120 may apply various intensity thresholding techniques to identify pleural lines and the boundaries thereof. Embodiments may also include one or more techniques for pleural line identification described in another related US patent application titled "Ultrasound System and Method for Detecting a Lung Sliding" and naming Wang, Shougang; Raju, Balasundar; Xu, JingPing; Zhou, Shiwei; Gades, Tony; and Poland, McKee, which is also incorporated by reference in its entirety herein.

The data processor 120 may be further configured to define a region of interest proximate one or more of the identified pleural lines. Narrowing the area within each image frame to a defined region of interest may minimize unnecessary processing and/or reduce the number of false positives, e.g., B-lines detected by the system 100 that are not actually B-lines. The region of interest may include the region below the pleural line, extending downward away from the ribs. The size of the region of interest may vary, and may be based at least in part on an average B-line length determined through a sample of B-line images and/or published clinical data. Because B-lines may be defined as the vertical lines that begin at the pleural line and extend to the bottom of the region of interest, regions of interest spanning an insufficient depth may be overly inclusive. Relative to the surface of the subject being imaged, the region of interest may extend to a depth of about 2 cm to about 8 cm, about 3 cm to about 6 cm, about 3 cm to about 5 cm, or about 2.5 cm to about 3.5 cm.

Within the region of interest, the data processor 120 may be configured to identify one or more candidate B-lines in each image frame. Candidates may include vertical, hyperechoic lines beginning at the pleural line. Out of the pool of candidate B-lines, the data processor 120 may identify legitimate B-line(s) by evaluating one or more parameters of each candidate, which may involve applying one or more B-line classification rules programmed into the data processor. Parameters may include the starting point of each candidate, the intensity of each candidate, the end location or length of each candidate, and/or any movement of each candidate detected across multiple image frames. These parameters are based on several B-line characteristics. For example, as mentioned, B-lines begin at the pleural line. Accordingly, the data processor 120 may exclude any vertical lines that do not begin at the pleural line. In addition, each B-line may extend to the bottom of the region of interest and may have a relatively uniform intensity along the length of the line, such that the line is coherent along its length and does not fade in some examples. B-lines may also have an approximately uniform width along the length of each line. The data processor 120 may be configured to measure each of these parameters within the image frames 119 by applying, in some examples, thresholding techniques to determine the borders of each B-line. The lateral width of each B-line candidate may be measured at various points along the length of each line, and the measured widths compared to determine whether candidate B-lines maintain an approximately equal width. The data processor 120 may also be configured to measure the intensity of each B-line via B-mode image processing. Comparing the intensity levels at multiple locations along the length of each individual B-line candidate may enable the data processor to evaluate the uniformity of B-line intensity. Candidates having a level of uniformity above a specified threshold may be selected as B-lines. Further, B-lines often move as a subject breathes. As a result, B-lines may appear in different positions between any two sequentially-collected frames. Candidate B-lines may thus be compared across multiple image frames to detect movement from frame to frame.

The data processor 120 may perform additional operations to determine the characteristics of one or more B-lines identified within each image frame. For example, the data processor 120 may determine the number of B-lines, the width of each B-line, the distance between one or more pairs of B-lines, and/or the width of the intercostal space (lateral distance between an adjacent pair of ribs) in each frame. In some examples, the data processor 120 may determine a B-line score. The B-line score may be calculated in various ways. For instance, some embodiments may involve calculating a B-line score by combining two or more measured parameters, e.g., width, intensity, uniformity, number, density, etc., and forming a composite value. In some embodiments, the B-line score may be based at least in part on the level of B-line coverage within at least one intercostal space. According to such examples, a higher B-line score may reflect a greater amount of B-line coverage, e.g., B-line coverage of 80% produces a higher B-line score than a B-line coverage of only 20% (see FIG. 4 for additional explanation).

The data processor may further select a target image frame for closer examination and/or display by identifying the image frame that maximizes a number and/or an intensity of B-lines relative to the other image frames generated. Of all the image frames collected at a specific location, the target image frame may be the frame with the strongest B-line presence, and may thus be the optimal image frame (compared to the other frames). Some examples may involve selecting a target image frame by identifying the image frame having the highest B-line score. In some embodiments, multiple target image frames may be selected, each target image frame corresponding to a discrete location on a subject's chest at which a series of image frames were collected. Each target image frame may thus correspond to a discrete sub-region that may be displayed on the user interface 124. The data processor 120 may be further configured to automatically save a copy of each target image frame to a memory storage device for later viewing. Archiving target image frames may also facilitate streamlined billing practices.

As further shown in FIG. 1, the system 100 may include at least one user interface 122. The user interface may be operatively, physically, and/or communicatively coupled with the ultrasound data acquisition unit 110 and the data processor 120. The user interface 122 may be configured to receive manual, electronic, and/or wireless input 128 from a user, which may include an indication of a location of the ultrasound probe with respect to the lung region of the subject. In some examples, the user interface 122 may include a touch screen. The user interface may be configured to display various images 124, including the target image frame identified by the data processor 120, and at least one indicator 126. In some embodiments, the user interface 122 may display the target image frame simultaneously with a real-time, e.g., live, ultrasound image obtained via ultrasound echoes being actively received at the sensor array 112. The target image frame may thus appear as a still image and the real-time image may be dynamic. To reduce or avoid overlap with the real-time image, the user interface 122 may display the target image frame adjacent to the real-time image. Displaying the images side-by-side in this manner may facilitate user interpretation of the real-time images by minimizing any interference that may result from superimposing the target image frame on the real-time image.

In some examples, the user interface 122 may also be configured to display two or more sub-regions within the region being scanned. As described above, the data processor 120 may be configured to identify one or more B-lines and a target image frame within each sub-region, each of which may be displayed by the user interface 122. For one or more of the sub-regions, the user interface 122 may display the number of B-lines detected by the data processor 120, their dimensions, start/end points, and/or intensity levels. Example user interfaces 122 may also display an indication of whether the number of B-lines exceeds a pre-determined threshold at any given sub-region. A B-line score may also be determined by the data processor 120 and displayed by the user interface 122 for each sub-region, such that a distribution of B-lines throughout the lung region may be displayed.

Figure 2A:
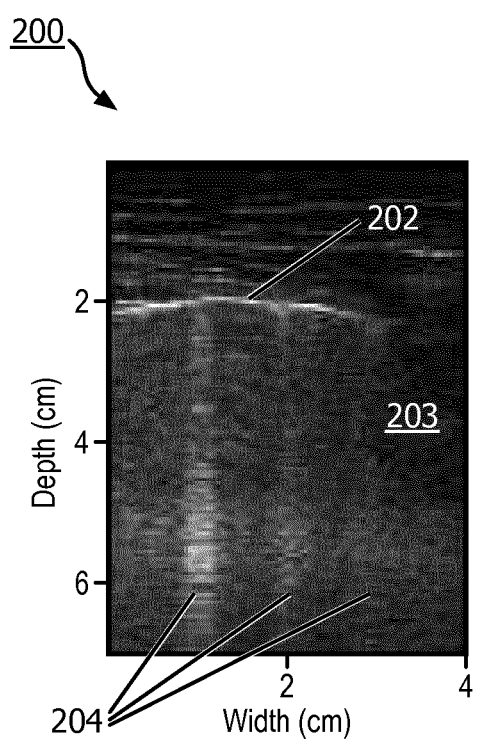
FIG. 2A is a lung ultrasound image taken with an ultrasound probe in accordance with the principles of the present disclosure.

FIGS. 2A-2D illustrate different aspects of the techniques employed by the system 100 to identify B-lines within an image frame. FIG. 2A is a B-mode image frame 200 that includes a pleural line 202, a region of interest 203 defined below the pleural line, and a plurality of candidate B-lines 204 within the region of interest. The image depth is displayed on the y-axis of the image, and the lateral width displayed on the x-axis. The image frame 200 may be generated by one or more processors, such as signal processor 118, in communication with an ultrasound data acquisition unit, e.g., data acquisition unit 110. As shown, the B-line candidates 204 may begin at the pleural line 202, at a depth of about 2 cm, and extend downward to a depth of approximately 7 cm.

Figure 2B:
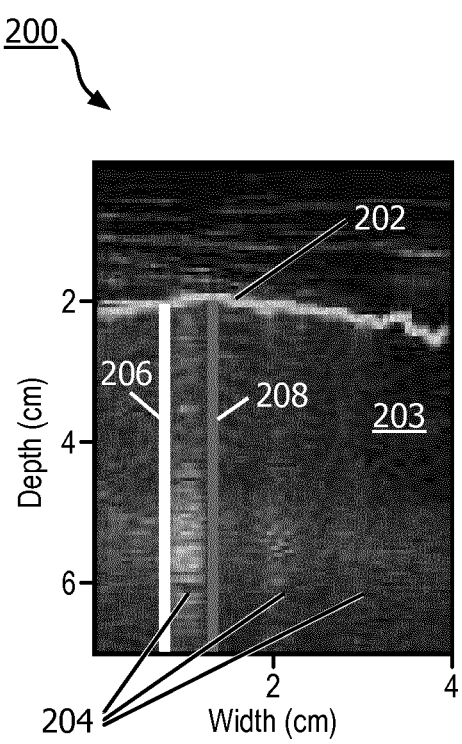
FIG. 2B is the lung ultrasound image of FIG. 2A including an indication of a pleural line and a B-line.

FIG. 2B illustrates the same image frame 200, including the pleural line 202 and the candidate B-lines 204. In FIG. 2B, the image frame 200 has been annotated such that the pleural line 202 and one of the candidate B-lines 204 has been identified. One or more processors, such as data processor 120, may be configured to identify these features on the image frame 200. In various examples, the data processor 120 may not actually mark the features on the image frame. Accordingly, the annotations shown in FIG. 2 may be provided for representation purposes only.

Figure 2C:
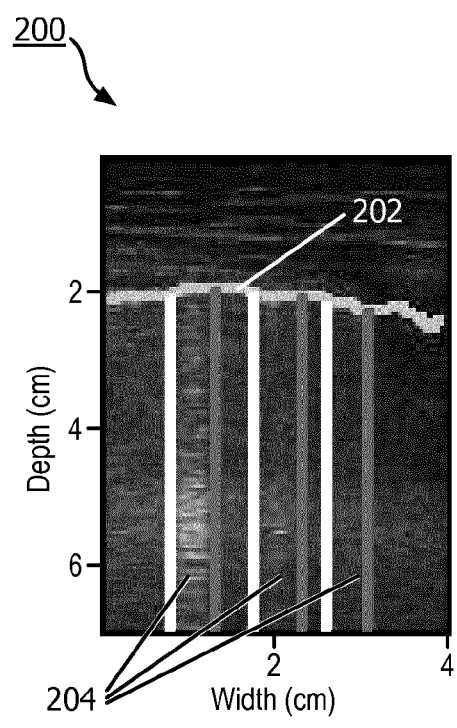
FIG. 2C is the lung ultrasound image of FIG. 2B including an indication of additional B-lines.

FIG. 2C also illustrates image frame 200, but with two additional B-line candidates 204 indicated. As shown, each of the candidate B-lines may appear as vertical, hyperechoic artifacts extending downward from the pleural line 202 into the region of interest 203.

Figure 2D:
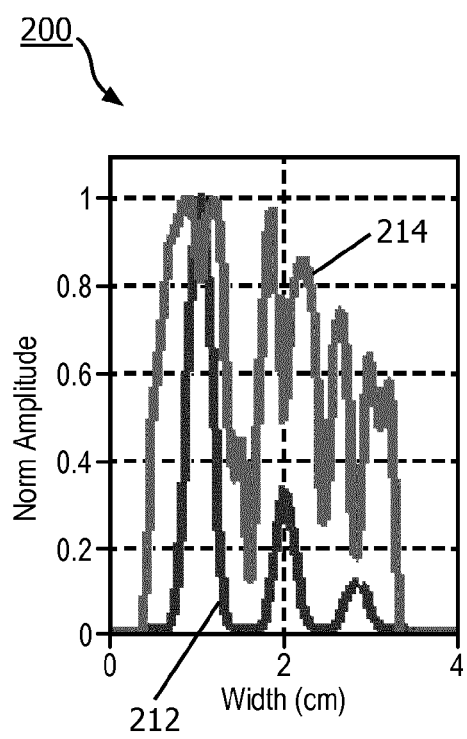
FIG. 2D is a graph indicating a width and amplitude of the B-lines indicated in FIG. 2C.

FIG. 2D illustrates a graph 210 of a primary axial projection ("total AP") curve 212 and an averaged cross correlation ("CC") coefficient curve 214 for the B-line candidates 204 shown in FIGS. 2A-2C. In some examples, data processor 120 may be configured to generate the total AP curve 212 and averaged CC coefficient curve 214 to identify candidate B-lines 204 by determining a similarity metric across depth within each image frame. For example, if B-lines exist within the region of interest, they will most likely appear as peaks on the total AP curve, which may also be identified by the data processor 120. In some embodiments, each region of interest 203 within a single image frame may be divided into sub-regions by the data processor 120. The number of sub-regions may vary, ranging from about 4 to about 20 in different embodiments. For each sub-region within the region of interest 203, the data processor 120 may compute a sub-AP curve and compute a normalized CC coefficient between every sub-AP curve and the total AP curve 212. Higher CC values, e.g., any values or ranges above 0.7, 0.8, 0.9 or greater, may be used to narrow the pool of B-line candidates, as such values indicate greater similarity between each of the sub-band AP curves and the total AP curve, a result that may reflect the signature coherent properties (width, intensity, etc.) across image depth indicative of typical B-lines. Each of the three B-line candidates 204 identified in FIG. 2C correspond to a single peak on the total AP curve depicted in FIG. 2D.

Determining the normalized CC coefficient may reduce or eliminate discrepancies in the system's interpretation of B-lines detected at focal zones of different depth. For example, some sonographers may prefer focal zones located approximately at the pleural line, while others prefer focal zones at a depth of about 4 cm. Focal zones at different depths may impact the uniformity of the B-lines appearing in the plurality of image frames. Because B-line uniformity may be a key characteristic of B-line interpretation, it may be imperative that any variation stemming from different focal depths does not influence B-line identification. Normalizing the CC coefficient values may eliminate or at least minimize discrepancies. Measuring the similarity in B-line intensity at different sub-bands may also distinguish B-lines having intensity levels similar to background intensity levels in a given image frame. Generally, candidate B-lines and in some examples, legitimate B-lines by computing intensity similarity metrics according to the foregoing approaches may reduce computation loads such that, in some examples, portable ultrasound systems may be capable of identifying B-lines and/or target image frames.

Figure 3A:
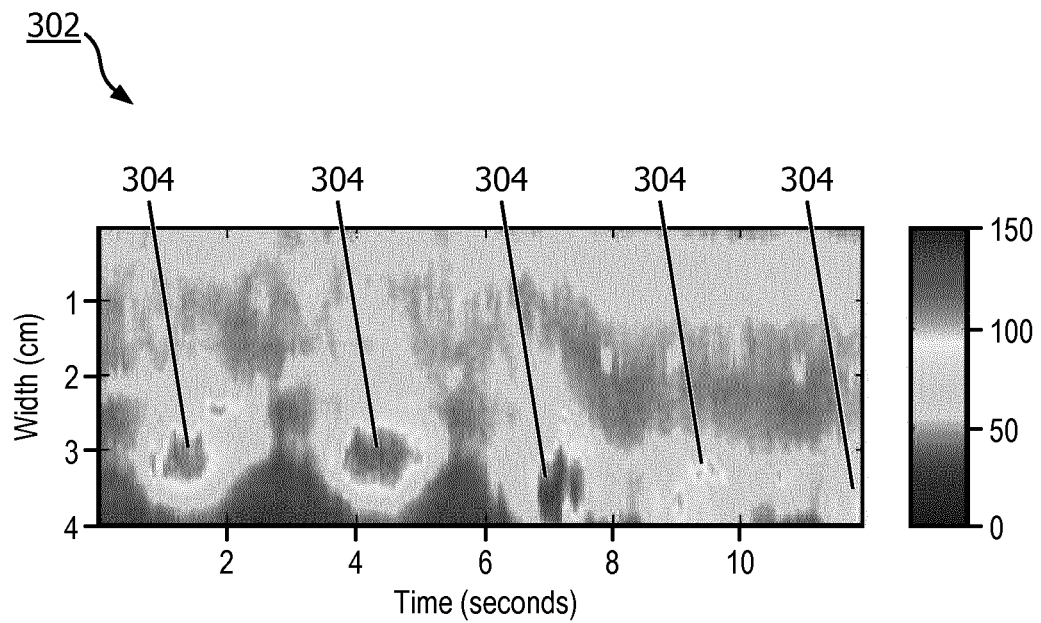
FIG. 3A is an intensity map of B-lines detected over time in a plurality of image frames.
Figure 3B:
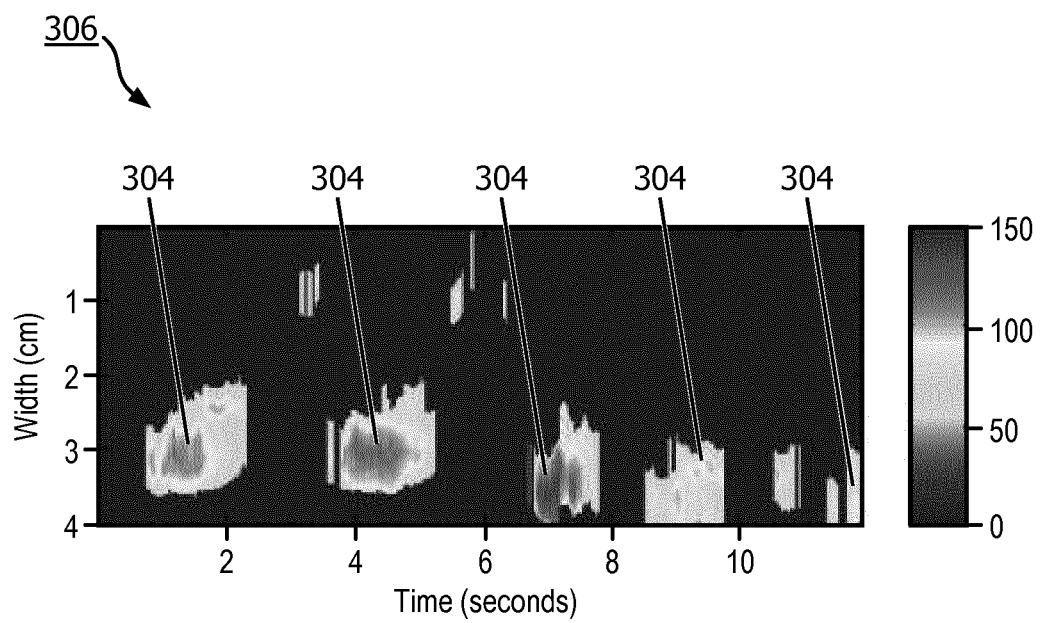
FIG. 3B is a line trace map of the intensity map shown in FIG. 3A.

FIGS. 3A and 3B illustrate graphical representations that may be produced, utilized, and/or displayed by the system 100 disclosed herein pursuant to selecting a target image frame from a plurality of image frames. In particular, FIGS. 3A and 3B illustrate the utilization of total intensity data gathered from a plurality of image frames to determine the time point, and depth, corresponding to the image frame of maximum overall intensity, which may correspond to the target image frame. FIG. 3A is an intensity map 302 showing axial intensity projections detected across multiple image frames as a function of lateral width (y-axis) and time (x-axis). As shown, the intensity map 302 includes multiple high-intensity regions 304. FIG. 3B is a line trace map 306 of the intensity map 302 shown in FIG. 3A, including the plurality of high-intensity regions 304. The line trace map 306 shows the location of axial intensity projections as a function of lateral width (y-axis) and time (x-axis). In line trace map 306, the image frames containing B-lines are indicated by removing variable shading from the axial intensity projections below a certain threshold. The threshold may thus be applied to eliminate areas of low intensity projection that likely do not represent image frames containing B-lines, or in some examples, image frames containing low numbers of B-lines or B-lines of low to moderate intensity.

In the examples shown, B-line intensity data is collected over a duration of about 12 seconds at a frame rate of 44 Hz, thus generating a total of 524 image frames, each of which is analyzed by data processor 120, for example, to determine axial intensity projection data for each frame. The intensity map shown in FIG. 3A thus represents a total axial projection curve map from all 524 image frames. The periodic pattern of B-line intensity portrayed in FIGS. 3A and 3B reflects the respiratory cycle. As shown, the strongest B-line intensity values are clustered around approximately 1.4 seconds. The target image frame selected by the data processor 120 may thus include the image frame generated at or near 1.4 seconds. One or more processors, such as data processor 120, may be configured to select the image frame generated at about 1.4 seconds, and communicate this image frame to a user interface, such as user interface 122, for display. In some examples, the image frame at 1.4 seconds may also be used to compute a B-line score. A target image frame may be selected over a fixed amount of time in some examples. In some embodiments, a target image frame may be selected over a fixed number of image frames and/or over a fixed number of respiration cycles. In addition or alternatively, the target image frame may be selected by summing the overall intensity levels of the all the pixels in a given image frame. The image frame with the highest summed intensity may represent the target image frame.

A user interface, such as user interface 122, may be configured to color-code areas of detected B-lines within a target image frame. The target image frame may be presented as a B-line trace map, such as the example shown in FIG. 3B, in some examples. Along with the location of each B-line, the user interface 122 may be configured to display the one or more B-line scores, a duration that each B-line remain across multiple image frames, and/or frame-to-frame differences in the B-line map.

Figure 4:
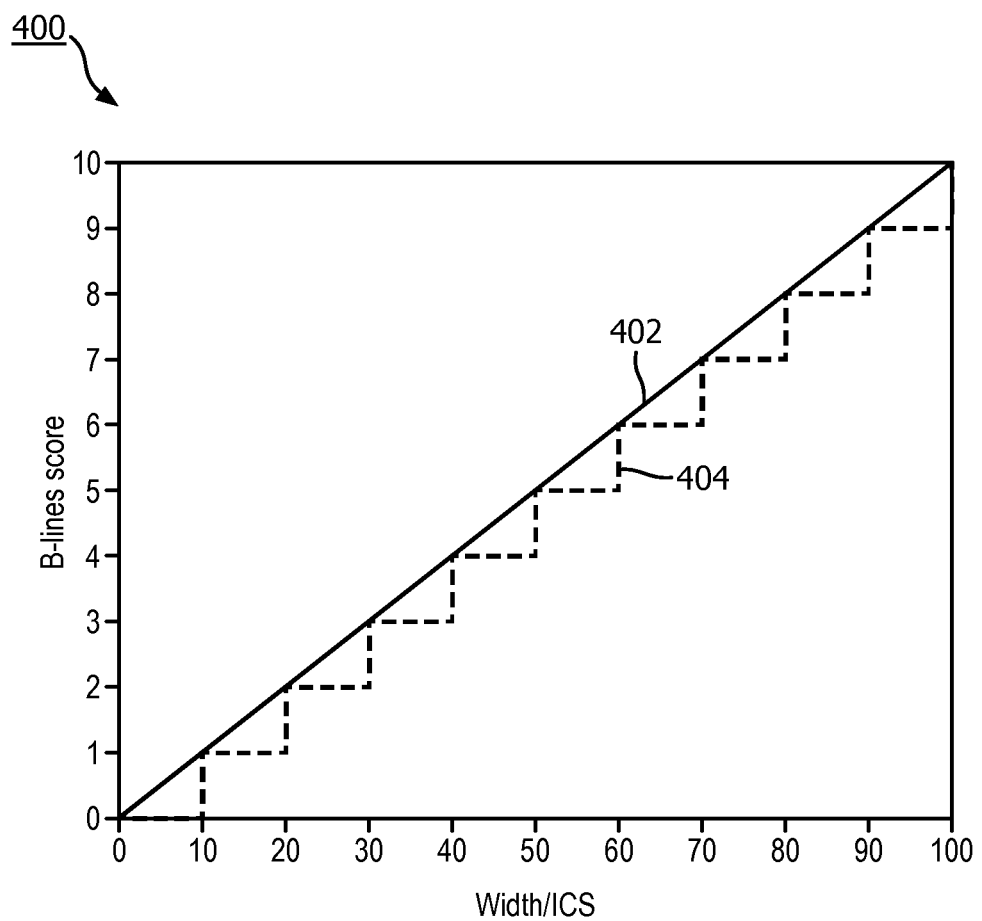
FIG. 4 is a graphical representation of a B-line scoring system.

FIG. 4 is a graphical representation of a B-line scoring system 400 according to embodiments of the present disclosure. The scoring system 400 is based on the proportion of B-line coverage within one or more intercostal spaces, and includes two variations: a linear scoring model 402 and a stepwise scoring model 404. Regardless of the specific scoring model employed, B-line(s) occupying the entirety of an intercostal space may be given the highest possible B-line score, e.g., 10, while the absence of B-lines within an intercostal score may correspond with the lowest possible B-line score, e.g., 0. Scores generated by the continuous model 402 may capture smaller variations in B-line coverage compared to the stepwise model 404. For instance, as shown in FIG. 4, the B-line score calculated according to the stepwise model remains constant between 20% and 30% B-line coverage, while the B-line score calculated over the same coverage range according to the continuous model 402 increases continuously as the proportion of B-line coverage increases.

Intercostal spaces may be determined according to various methods. For example, during a longitudinal scan, an intercostal space may be defined as the width between two adjacent ribs based on the actual length of the pleural line spanning the intercostal space, or the between the two boundaries of the shadows created by the ribs. For transverse scans, an intercostal space may be defined as the actual length of the pleural line shown on a B-mode image.

In some examples, one or more B-line scores may be calculated based on the number of discrete B-lines present within one or more intercostal spaces. In such examples, a discrete B-line width may be defined. The standard width of a single B-line may be defined as, for instance, less than 50% of the width of the intercostal space, which may be approximately 2 cm. The number of discrete B-lines having a width of less than 50% may be equal to, or directly related to, the overall B-lines score. For example, 4 B-lines detected within a single intercostal space may correspond to a B-line score of 4 (on a scale of 1 to 10). B-lines of greater width may indicate fused and/or confluent B-lines, which may be assigned a score based on the fused/confluent width. For instance, if the width is greater than 50%, but less than 75% of the intercostal space, the fused and/or confluent B-line may be assigned a score of 6. If the width is greater than 75%, but less than 100%, the fused/confluent B-line may be given a score of 7. If the width is 100% of the intercostal space, then the fused/confluent B-line may be given a score of 8, and so on.

Figure 5A:
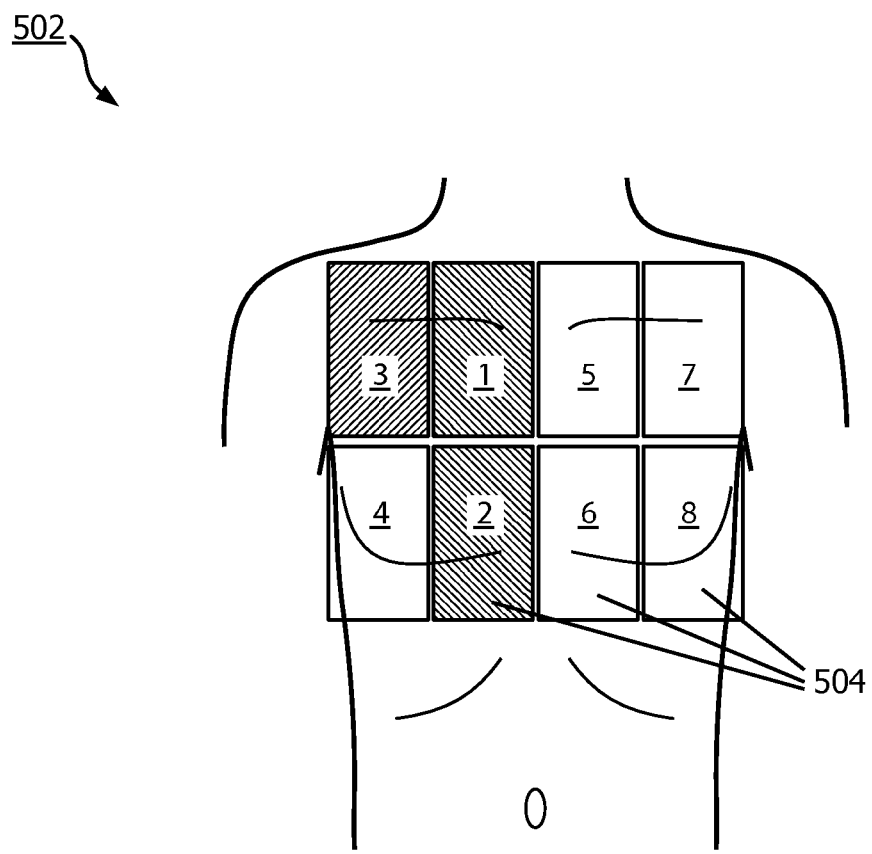
FIG. 5A is a diagram of multiple sub-regions within a region of interest of a subject.
Figure 5B:
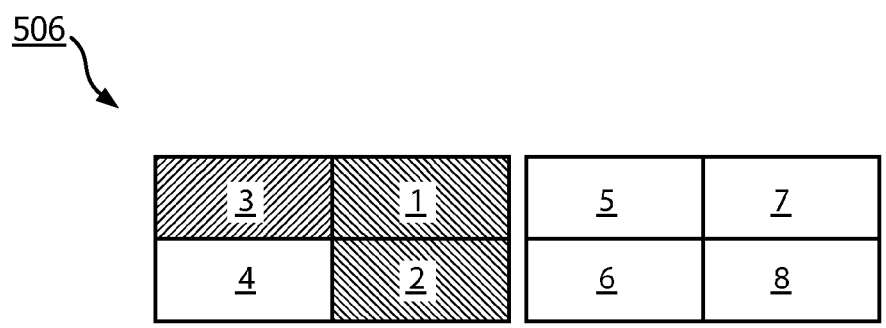
FIG. 5B is a table reporting qualitative B-line scores for regions of interest shown in FIG. 5A.

FIG. 5A is a diagram of multiple zones or sub-regions within a region of interest of a subject. The diagram 502 shown in FIG. 5A may be generated and displayed on a user interface, for example user interface 122. The diagram 502 includes a schematic of the chest region of a subject, which is divided into 8 separate zones or sub-regions 504. One or more sub-regions 504 may be selectable by a user, e.g., via a touch interface. Upon selecting a sub-region 504, the user interface 122 may display various types of statistical information regarding the B-lines detected within that particular sub-region, e.g., the number of B-lines detected and/or one or more B-line scores. The particular embodiment shown in FIG. 5A includes 8 sub-regions 504. More or fewer than 8 sub-regions may be included in some examples. Three of the sub-regions 504 (sub-regions #1, #2 and #3) shown in FIG. 5A may be shaded a different color than the rest of the sub-regions. This may indicate, in some embodiments, that these three zones have already been selected for examination by a user. FIG. 5B is a table reporting a qualitative B-line score for each sub-region shown in FIG. 5A. The table 506 may report B-line scores by assigning different colors to different scores. For example, sub-region #3 may be shaded red to indicate a high B-line score, e.g., a score equal to or greater than 5. By contrast, sub-regions #1 and #2 may be shaded green or blue to indicate a low B-line score, e.g., a score equal to or greater than 0 but less than 3. Color coding may be determined by a data processor, e.g., data processor 120.

FIG. 5C is a table reporting a quantitative B-line score for each region of interest shown in FIG. 5A. The example table 508 shown in FIG. 5C includes 3 columns: a first column indicating the sub-region numbers shown in the diagram 502 illustrated in FIG. 5A, a second column indicating the number of B-lines detected at the particular sub-region numbers, and a third column showing the calculated B-line score for each sub-region on a scale of 1 to 10. Consistent with the table 506 shown in FIG. 5B, table 508 confirms that zone #3 includes the highest B-line score (6) of the sub-regions evaluated. The quantitative data included in table 508 may inform estimations of extravascular lung water and/or may facilitate precise monitoring of a condition, e.g., pulmonary edema, over time.

One or more of FIGS. 5A-5C may be displayed on a given user interface simultaneously. In some examples, a user may toggle between images on the user interface, for example switching between a table view, a diagram view, a quantitative view, a qualitative view, and/or a live image feed. In some embodiments, a user interface may be configured to receive manual input directly into one or more tables, such as the table 508 shown in FIG. 5C. After populating a table containing B-line information, the table may be archived for later viewing.

Figure 6:
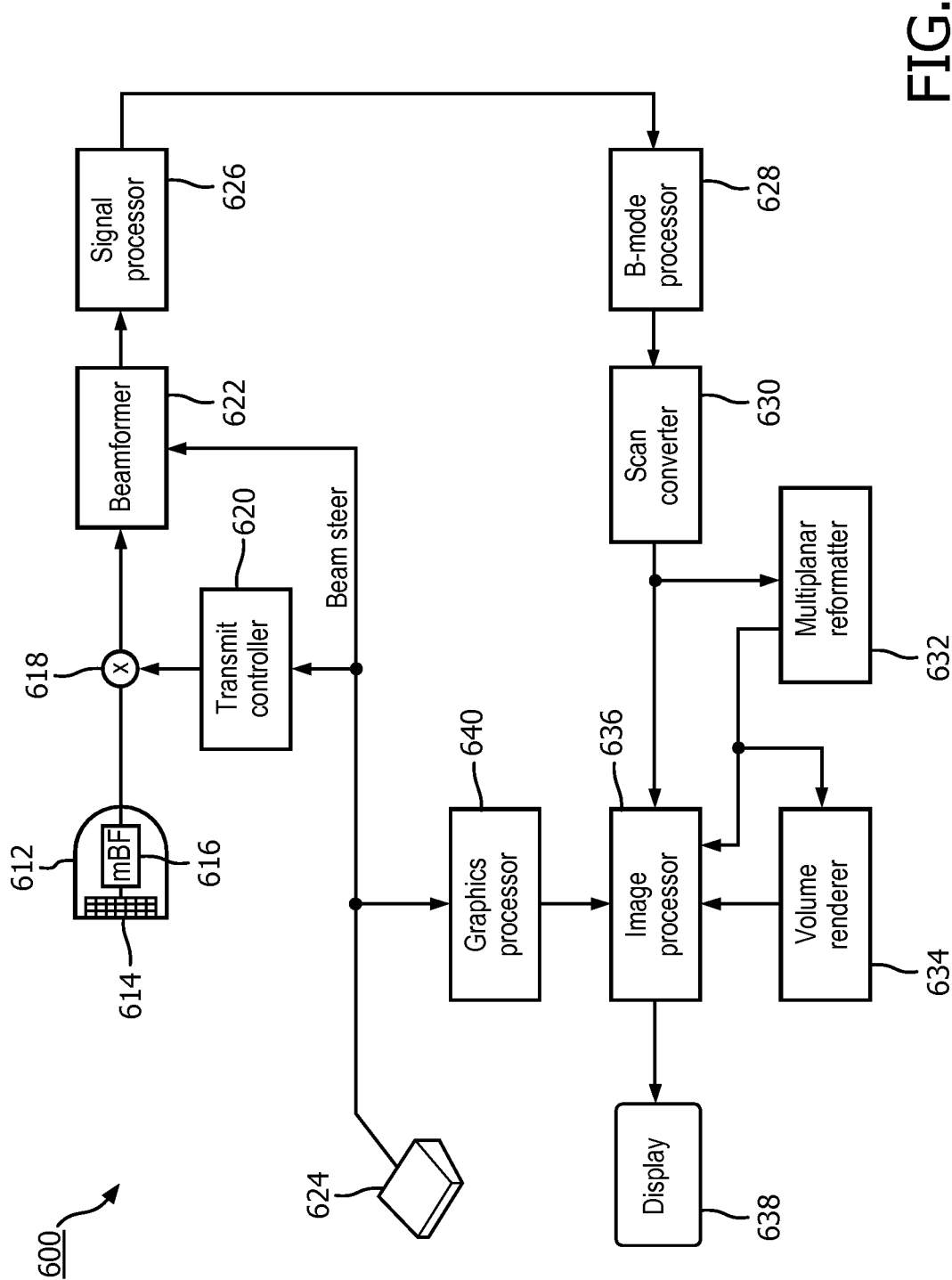
FIG. 6 is a block diagram of an ultrasound imaging system in accordance with the principles of the present disclosure.

FIG. 6 illustrates an ultrasound imaging system 600 constructed in accordance with the principles of the present invention. One or more components shown in FIG. 6 may be included within a system configured to identify B-lines within a region of a subject, select a target image frame containing an image of the B-lines, and/or display the target image frame, along with B-line scores and/or statistics, to a user. For example, any of the above-described functions of the signal processor 118 and the data processor 120 may be programmed, e.g., via computer executable instructions, into an existing processor of the system 600. In some examples, the functions of the data processor 120 may be implemented and/or controlled by one or more of the processing components shown in FIG. 6, including for example, the B-mode processor 628, scan converter 630, multiplanar reformatter 632, volume renderer 634 and/or image processor 636.

In the ultrasonic imaging system of FIG. 6, an ultrasound probe 612 includes a transducer array 614 for transmitting ultrasonic waves into a region containing the lungs and receiving echo information responsive to the transmitted waves. The transducer array 614 may be a matrix array that includes a plurality of transducer elements configured to be individually activated. In other embodiments, the transducer array 614 may be a one-dimensional linear array. The transducer array 614 is coupled to a microbeamformer 616 in the probe 612 which may control the transmission and reception of signals by the transducer elements in the array. In the example shown, the microbeamformer 616 is coupled by the probe cable to a transmit/receive (T/R) switch 618, which switches between transmission and reception and protects the main beamformer 622 from high energy transmit signals. In some embodiments, the T/R switch 618 and other elements in the system can be included in the transducer probe rather than in a separate ultrasound system base. The transmission of ultrasonic beams from the transducer array 614 under control of the microbeamformer 616 is directed by the transmit controller 620 coupled to the T/R switch 618 and the beamformer 622, which receives input, e.g., from the user's operation of the user interface or control panel 624. One of the functions controlled by the transmit controller 620 is the direction in which beams are steered. Beams may be steered straight ahead from (orthogonal to) the transducer array, or at different angles for a wider field of view. The partially beamformed signals produced by the microbeamformer 616 are coupled to a main beamformer 622 where partially beamformed signals from individual patches of transducer elements are combined into a fully beamformed signal.

The beamformed signals are coupled to a signal processor 626. Signal processor 626 may process the received echo signals in various ways, such as bandpass filtering, decimation, I and Q component separation, and harmonic signal separation. Data generated by the different processing techniques employed by the signal processor 626 may be used by a data processor to identify pleural lines, B-lines, or internal structures, e.g., ribs, and parameters thereof. The signal processor 626 may also perform additional signal enhancement such as speckle reduction, signal compounding, and noise elimination. The processed signals may be coupled to a B-mode processor 628, which can employ amplitude detection for the imaging of structures in the body, including the ribs, the heart, and/or the pleural interface, for example. The signals produced by the B-mode processor are coupled to a scan converter 630 and a multiplanar reformatter 632. The scan converter 630 arranges the echo signals in the spatial relationship from which they were received in a desired image format. For instance, the scan converter 630 may arrange the echo signals into a two dimensional (2D) sector-shaped format. The multiplanar reformatter 632 can convert echoes which are received from points in a common plane in a volumetric region of the body into an ultrasonic image of that plane, as described in U.S. Pat. No. 6,443,896 (Detmer). A volume renderer 634 converts the echo signals of a 3D data set into a projected 3D image as viewed from a given reference point, e.g., as described in U.S. Pat. No. 6,530,885 (Entrekin et al.). The 2D or 3D images are coupled from the scan converter 630, multiplanar reformatter 632, and volume renderer 634 to an image processor 636 for further enhancement, buffering and temporary storage for display on an image display 638. The graphics processor 636 can generate graphic overlays for display with the ultrasound images. These graphic overlays can contain, e.g., standard identifying information such as patient name, date and time of the image, imaging parameters, and the like, and also various B-line statistics and/or B-line scores. Graphic overlays may also include one or more signals indicating the target image frame has been obtained and/or the system 600 is in the process of identifying the target image frame. The graphics processor may receive input from the user interface 624, such as a typed patient name. The user interface 624 may also receive input prompting adjustments in the settings and/or parameters used by the system 600. The user interface can also be coupled to the multiplanar reformatter 632 for selection and control of a display of multiple multiplanar reformatted (MPR) images.

Figure 7:
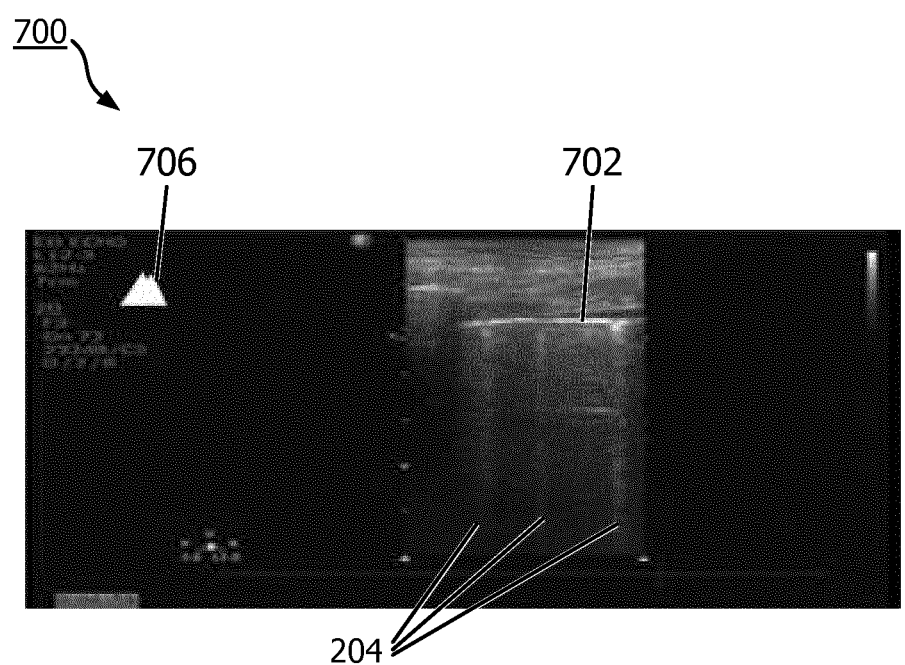
FIG. 7 is a lung ultrasound image taken at a target image frame in accordance with the principles of the present disclosure.

FIG. 7 is a lung ultrasound image 700 of a lung region taken at a target image frame selected according to the embodiments described herein. The image 700 shown in FIG. 7 may be obtained with a linear array transducer in a tissue-harmonic imaging mode. The image 700 includes a pleural line 702 and three B-lines 704, each B-line beginning at the pleural line 702 and extending downward. FIG. 7 also depicts an example of an indicator 706 displayed on the screen to provide one or more indications regarding the detected B-lines and/or the implications of such B-lines. In various examples, the indicator 706 may indicate to a user that the target image frame is being displayed. The indicator 706 may indicate to a user that the number of B-lines depicted in the image 700 satisfies one or more threshold numbers of B-lines. For example, the number of B-lines may indicate the existence and/or volume of extravascular lung water. The indicator 706 may appear and/or undergo a change in appearance if 3 or more B-lines are identified in a given image, for example, to alert a user that extravascular lung water may be present within the lungs. In some embodiments, the indicator 706 may indicate to a user that the lung region depicted in the image is either normal or abnormal. The indicator 706 may comprise an absolute, binary signal that either appears on the image or does not appear, or the indicator 706 may provide a gradual signal that changes based on the intensity of the B-lines included in an image frame. For example, as the number of B-lines increase above a certain threshold, the severity of extravascular lung water may intensify. The indicator 706 may reflect this gradual change in intensity by changing in brightness or color, for example. In some embodiments, the indicator 706 may not include a displayed graphic at all, instead including an audio cue and/or tactile stimulation, for example. In some examples, additional information may be displayed on the image 700. For example, an indication of whether the number of B-lines shown in the image 700 satisfies a given threshold may be included.

The information conveyed in a target image frame, such as that depicted in FIG. 7, may be utilized pursuant to a variety of applications. For example, PTX may be diagnosed with up to 100% specificity based on the presence or absence of B-lines at a given location. Specifically, the presence of B-lines may be used to rule out the possibility of diagnosing a patient with PTX. Various fluid therapies may also be guided with information regarding extravascular lung water volumes and locations determined based on the number of B-lines, width of B-lines, and/or average distances between any pair of B-lines.

Figure 8:
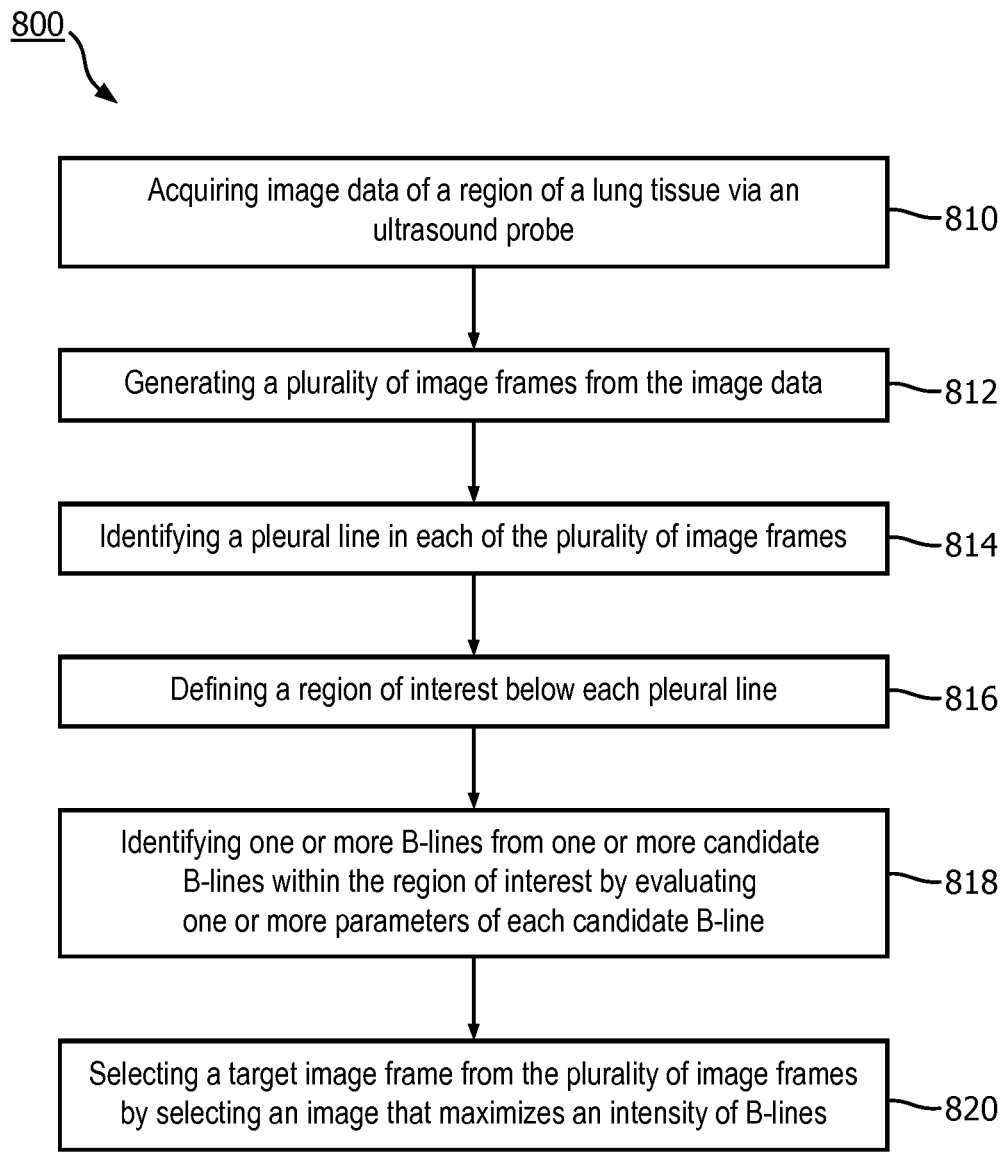
FIG. 8 is a block diagram of an ultrasound imaging method in accordance with principles of the present disclosure.

FIG. 8 is a block diagram of an ultrasound imaging method in accordance with the principles of the present disclosure. The example method 800 of FIG. 8 shows the steps that may be utilized, in any sequence, by the systems and/or apparatuses described herein for identifying B-lines and selecting a target image frame containing the B-lines for display. The method 800 may be performed by an ultrasound imaging system, such as system 800, or other systems including, for example, a mobile system such as LUMIFY by Koninklijke Philips N. V. ("Philips"). Additional example systems may include SPARQ and/or EPIQ, also produced by Philips.

In the embodiment shown, the method 800 begins at block 810 by "acquiring image data of a region of a lung tissue via an ultrasound probe." Image data may be gathered via an ultrasound data acquisition unit, which may contain various configurations of sensor arrays, including those described above with respect to FIG. 1. The region may span the entire chest region or at least one or more portions thereof. One or more locations within the region may be targeted by a user operating the ultrasound data acquisition unit if such locations have been identified previously as harboring one or more abnormalities, example a pulmonary edema and/or extravascular lung water.

At block 812, the method involves "generating a plurality of image frames from the image data." The image frames may be generated by processing ultrasound echoes received at the data acquisition unit. A collection of image frames may be collected in series at various discrete locations throughout the region of the lung tissue being imaged. One or more of the image frames may be captured and stored by one or more devices configured to perform the method 800. One or more of the image frames may include at least one pleural line and one or more B-lines. In some examples, none of the image frames may include a B-line.

At block 814, the method involves "identifying a pleural line in each of the plurality of image frames." Various techniques may be employed, for example by a data processor, to identify pleural lines. Such techniques may apply intensity thresholding to identify the presence and/or boundaries of one or more pleural lines.

At block 816, the method involves "defining a region of interest below each pleural line." The region of interest includes the area beneath, i.e., at greater depths, the pleural line. If one or more B-lines are present in a given image frame, the B-lines will appear beneath the pleural line. Regions of interest may be of uniform dimensions in some examples. In some embodiments, the size of the regions of interest may vary across multiple image frames and/or across various implementations of the method 800.

At block 818, the method involves "identifying one or more B-lines from one or more candidate B-lines within the region of interest by evaluating one or more parameters of each candidate B-line." In some examples, candidates may be identified by determining an intensity similarity metric across depth within each image frame. In some embodiments, candidate B-lines may be selected by measuring axial intensity projection data across one or more sub-regions within the region of interest defined within each individual image frame. Cross correlation coefficients may be normalized across multiple sub-bands to evaluate the likelihood that peaks in the axial projection intensity data correspond to B-lines. In some embodiments, B-lines may be identified by measuring one or more parameters indicative of most B-lines. In various examples, the parameters may include an intensity uniformity level, a length, a starting location, an ending location, and/or a level of the motion detected. For instance, B-lines typically begin at the pleural line. In addition, B-lines commonly appear uniform in intensity and dimension along the length of each B-line. B-lines may also extend from the pleural line to the bottom of the region of interest.

At block 820, the method involves "selecting a target image frame from the plurality of image frames by selecting an image frame that maximizes an intensity of B-lines." In some examples, the target image frame may be the frame having the highest calculated B-line score within a series of image frames. The B-line score may be based on the proportion of an intercostal space covered by one or more B-lines. The target image frame may correspond to the image frame having the highest overall intensity compared to a plurality of image frames.

The method 800 may further involve, for example, displaying the target image frame simultaneously with a real-time image of the lung tissue and/or comparing two or more image frames to detect motion of one or more candidate B-lines. In some embodiments, the method 800 may also involve determining an intercostal space between each pair of ribs within the region of interest, determining a proportion of each intercostal space that is covered by one or more B-lines, and generating a B-line score based on the proportion for each intercostal space. Such methods may also involve generating and displaying a pictorial representation of multiple B-line scores, each B-line score corresponding to a sub-region within the region of the lung tissue.

Of course, it is to be appreciated that any one of the examples, embodiments or processes described herein may be combined with one or more other examples, embodiments and/or processes or be separated and/or performed amongst separate devices or device portions in accordance with the present systems, devices and methods. The above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

The invention claimed is:

1. An ultrasound imaging system comprising:
   an ultrasound probe configured to receive ultrasound echoes from a subject to image a lung region of the subject;
   a processor, in communication with the ultrasound probe, configured to:
      generate a plurality of image frames from the ultrasound echoes as the ultrasound probe is receiving the ultrasound echoes;
      identify a pleural line in each of the plurality of image frames;
      define a region of interest as an area contained within each of the plurality of image frames below each pleural line;
      identify one or more B-lines from one or more candidate B-lines within the region of interest by evaluating a plurality of parameters of each candidate B-line within the region of interest in each of the plurality of image frames, wherein the plurality of parameters includes a length of the B-line and an intensity uniformity level along the length of the B-line, wherein candidate B-lines having the intensity uniformity level above a specified threshold are identified as the one or more B-lines;
      select a target image frame from the plurality of image frames by identifying an image frame providing a maximal intensity of identified B-lines, wherein the maximal intensity is determined based on axial intensity projection data for each of the plurality of image frames as a function of a lateral width of the identified B-lines and a time; and
      compute, for the target image frame, a B-line score based at least in part on a level of B-line coverage within at least one intercostal space present within the region of interest; and
   a user interface in communication with the processor, the user interface configured to display the target image frame simultaneously with a real-time image responsive to the ultrasound echoes received at the ultrasound probe.

2. The ultrasound imaging system of claim 1, wherein the plurality of parameters comprise at least one of a starting location of each of the one or more candidate B-lines, an ending location of each of the one or more candidate B-lines, or a level of motion detected across multiple image frames of each of the one or more candidate B-lines.

3. The ultrasound imaging system of claim 1, wherein the user interface is configured to display two or more sub-regions selectable by a user, each sub-region corresponding to a portion of the lung region of the subject.

4. The ultrasound imaging system of claim 3, wherein the processor is further configured to identify one or more B-lines and a target frame within each sub-region.

5. The ultrasound imaging system of claim 4, wherein for each sub-region, the user interface is configured to display one or more of a number of B-lines, an indication of whether the number of B-lines exceeds a pre-determined threshold, or a starting and ending location of each B-line.

6. The ultrasound imaging system of claim 4, wherein the processor is further configured to determine a B-line score for each sub-region, the B-line score based at least in part on a level of B-line coverage within at least one intercostal space present within each sub-region.

7. The ultrasound imaging system of claim 6, wherein the user interface is configured to provide an indication of the B-line score and an indication of whether the B-line score is normal or abnormal for each sub-region such that a distribution of B-lines throughout the lung region is displayed.

8. The ultrasound imaging system of claim 1, wherein the intensity of B-lines comprises at least one of a number of B-lines or a width of one or more B-lines.

9. A method comprising:
   acquiring image data of a region of a lung tissue via an ultrasound probe;
   generating a plurality of image frames from the image data;
   identifying a pleural line in each of the plurality of image frames;
   defining a region of interest as an area contained within the image frame below each pleural line;
   identifying one or more B-lines from one or more candidate B-lines within the region of interest by evaluating a plurality of parameters of each candidate B-line within the region of interest in each of the plurality of image frames, wherein the plurality of parameters comprises a length of the B-line and an intensity uniformity level along the length of the B-line, wherein candidate B-lines having the intensity uniformity level above a specified threshold are identified as the one or more B-lines;
   selecting a target image frame from the plurality of image frames by:
      determining axial intensity projection data for each of the plurality of image frames as a function of a lateral width of the identified B-lines and a time,
      identifying a time point corresponding to a maximal intensity of B-lines using the axial intensity projection data, and
      selecting the target image frame based at least in part on the identified time point;
   computing a B-line score for the target image frame, the B-line score based at least in part on a level of B-line coverage within at least one intercostal space present within the region of interest; and
   displaying the target image frame on a user interface in communication with the processor simultaneously with a real-time image responsive to the ultrasound echoes received at the ultrasound probe.

10. The method of claim 9, further comprising comparing two or more image frames to detect motion of one or more candidate B-lines.

11. The method of claim 10, wherein the plurality of parameters further comprises at least one of a starting location of each of the one or more candidate B-lines, an ending location of each of the one or more candidate B-lines, or a level of the motion detected of each of the one or more candidate B-lines.

12. The method of claim 9, wherein the level of B-line coverage is determined by:
   identifying an intercostal space between at least one pair of ribs within the region of interest;
   determining a proportion of the intercostal space covered by one or more B-lines; and
   generating the B-line score based on the proportion.

13. The ultrasound imaging system of claim 1, wherein the target image frame is a still image and the real-time image is dynamic.

14. The ultrasound imaging system of claim 1, wherein the processor is further configured to reduce a computation load of the ultrasound imaging system by generating an averaged cross correlation coefficient curve to identify candidate B-lines by determining a similarity metric across depth within each image frame.

15. The method of claim 9, further comprising displaying on the user interface an indication of whether the number of B-lines exceeds a pre-determined threshold.

* * * * *